US009545229B2

(12) United States Patent
Whitfield

(10) Patent No.: US 9,545,229 B2
(45) Date of Patent: *Jan. 17, 2017

(54) HEART MONITORING DEVICE

(71) Applicant: Jonathan M. Whitfield, Dallas, TX (US)

(72) Inventor: Jonathan M. Whitfield, Dallas, TX (US)

(73) Assignee: Jonathan M. Whitfield, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/753,731

(22) Filed: Jun. 29, 2015

(65) Prior Publication Data

US 2015/0297147 A1    Oct. 22, 2015

Related U.S. Application Data

(63) Continuation of application No. 14/189,144, filed on Feb. 25, 2014, now Pat. No. 9,066,665, which is a
(Continued)

(51) Int. Cl.
*A61B 5/02* (2006.01)
*A61B 5/00* (2006.01)
(Continued)

(52) U.S. Cl.
CPC ............. *A61B 5/743* (2013.01); *A61B 5/024* (2013.01); *A61B 5/02444* (2013.01);
(Continued)

(58) Field of Classification Search
CPC . A61B 2503/06; A61B 5/024; A61B 5/02444; A61B 5/4839; A61B 5/7275; A61B 5/7278; A61B 5/7282; A61B 5/743; A61B 5/7475; A61B 7/02; A61B 7/04
See application file for complete search history.

(56) References Cited

U.S. PATENT DOCUMENTS 5,421,830 A * 6/1995 Epstein et al. ............... 607/30
6,210,344 B1   4/2001 Perin et al.
(Continued)

FOREIGN PATENT DOCUMENTS

GB    WO2004075750    9/2004

OTHER PUBLICATIONS

Written Opinion of the International Searching Authority (PCT Rule 43bis.1), Patent Cooperation Treaty.

*Primary Examiner* — George Manuel
(74) *Attorney, Agent, or Firm* — DeLio, Peterson & Curcio, LLC

(57) ABSTRACT

The present invention includes devices, methods and systems for reporting a heart rate comprising: an input device; a microprocessor coupled to the input device and a power supply, wherein the microprocessor is programmed with a predetermined heartbeat threshold and calculates the number of times the input device is actuated over a predetermined amount of time; and a display connected to the microprocessor that receives the calculated heart rate and displays whether the heart rate is below, at or above predetermined threshold, e.g., when a patient has less than 60 heartbeats per minute, between 60 and 100 heartbeats per minute and greater than 100 heartbeats per minute.

19 Claims, 13 Drawing Sheets

Related U.S. Application Data continuation of application No. 13/680,323, filed as application No. PCT/US2011/036029 on May 11, 2011, now Pat. No. 8,696,587.

(60) Provisional application No. 61/347,733, filed on May 24, 2010.

(51) Int. Cl.
*A61B 5/024* (2006.01)
*A61B 7/02* (2006.01)
*A61B 7/04* (2006.01)

(52) U.S. Cl.
CPC .......... *A61B 5/7275* (2013.01); *A61B 5/7278* (2013.01); *A61B 5/7282* (2013.01); *A61B 5/7475* (2013.01); *A61B 7/02* (2013.01); *A61B 7/04* (2013.01); *A61B 5/4839* (2013.01); *A61B 2503/06* (2013.01)

(56) References Cited

U.S. PATENT DOCUMENTS

| | | |
|---|---|---|
| 6,491,647 B1 | 12/2002 | Bridger et al. |
| 7,539,532 B2 * | 5/2009 | Tran .............................. 600/509 |
| 7,880,607 B2 * | 2/2011 | Olson et al. .................. 340/521 |
| 2002/0097155 A1 | 7/2002 | Cassel et al. |
| 2004/0249298 A1 | 12/2004 | Selevan |
| 2009/0275848 A1 | 11/2009 | Brockway et al. |
| 2012/0029300 A1 | 2/2012 | Paquet |

* cited by examiner

HEART MONITORING DEVICE

RELATED APPLICATIONS

This application is a continuation of U.S. application Ser. No. 14/189,144 filed Feb. 25, 2014, which is a continuation of U.S. application Ser. No. 13/680,323 filed Nov. 19, 2012, which is a 371 to PCT Application No. PCT/US2011/036029 filed May 11, 2011, which claims priority to U.S. Provisional Application No. 61/347,733 filed on May 24, 2010.

BACKGROUND OF THE INVENTION

1. Field of the Invention

The present invention relates in general to the field of heart monitoring, and more particularly, to a device, method and system for determining and outputting in real-time the heart rate of a patient.

2. Description of Related Art

Without limiting the scope of the invention, its background is described in connection with heart monitoring devices.

One example of a heart-monitoring device is taught in U.S. Pat. No. 6,210,344, issued to Perin, et al., for a method and apparatus for passive heart rate detection. Briefly, this reference teaches a method and apparatus for measuring the heart rate of a patient, which includes a hollow bell mounted on a diaphragm. A transducer element is positioned to receive sound transmitted through the diaphragm, convert the sounds into electrical impulses, and transmit the electrical impulses to a microprocessor. The electrical impulses have real-time wave patterns corresponding to the real-time wave patterns of the original sounds. The microprocessor performs mathematical operations on wave pattern data conveyed by the electrical impulses to determine a numerical value corresponding to the frequency of the wave patterns. This numerical value is sent to a digital output and displayed thereon.

U.S. Pat. No. 5,218,969, issued to Bredesen, et al., discloses an intelligent stethoscope. This intelligent stethoscope is used for performing auscultation and for automatically diagnosing abnormalities based on body sounds wherein the body sounds are received, digitized and stored in memory. The body sounds are recorded from a plurality of locations on the body, and all of the sounds are categorized according to specific characteristics to form a matrix of information. The generated matrix is then compared against a plurality of stored matrices using a technique similar to analysis. Each of the stored matrices contain information indicative of known abnormalities such as specific heart murmurs, lung abnormalities, etc. When a matrix match is found, the diagnosis is displayed on an LCD display formed in the body of the stethoscope. The LCD display is also capable of displaying a visual representation of the recorded body sounds.

Still another prior art reference, U.S. Pat. No. 4,436,096, issued to Dyck, et al., discloses a portable digital heart rate meter/stethoscope. This prior art reference discloses that electrical signals corresponding to heart sounds detected by a pulse/sound transducer are filtered in a narrow band pass filter, whose pass band is centered on a characteristic heart sound frequency of 33 Hz. The filter improves signal-to-noise ratio and enables the transducer to be used over a patient's clothing. The unfiltered signal is amplified and fed to binaural leads to provide the function of an electronic stethoscope. In addition, the filtered signal is converted into pulses in response to which a count corresponding to the detected heart rate is established in a counter and displayed as a digital heart rate indication.

While known heart monitoring devices are useful after baseline information has been attained, they are not useful when time is of the essence and only a hands-on auscultation is reliable. Furthermore, such known heart monitoring devices do not allow the entire medical team to have a comprehensive awareness of the medical condition of the patient in an immediate and reliable manner.

SUMMARY OF THE INVENTION

The present invention relates in general to the field of heart monitoring, and more particularly, to devices, methods and systems for determining and outputting in real-time the heart rate of a patient.

In one or more embodiments, the invention includes devices for reporting a heart rate comprising: an input device; a microprocessor coupled to the input device and a power supply, wherein the microprocessor may be programmed with predetermined heartbeat thresholds and calculates the number of times the input device is actuated over a predetermined amount of time to generate a calculated heart rate; and a display connected to the microprocessor that receives the calculated heart rate and outputs the calculated heart rate along with a unique identifier identifying whether the calculated heart rate is below, at or above the predetermined heartbeat thresholds. The microprocessor coupled is also preferably coupled to a power supply.

In further embodiments, the invention is directed to methods for calculating a neonatal heart rate the utilizes a device for inputting data that includes an input device; a microprocessor coupled to the input device, wherein the microprocessor is programmed with predetermined heartbeat thresholds and calculates the number of times the input device is actuated over a predetermined amount of time to generate a calculated heart rate; and the device includes a display connected to the microprocessor that receives the calculated heart rate and outputs the calculated heart rate along with a unique identifier identifying whether the calculated heart rate is below, at or above the predetermined heartbeat thresholds. The methods for calculating a neonatal heart rate include placing a stethoscope on a neonatal patient; providing the device for inputting data each time a heartbeat is auscultated; actuating the input device each time the heartbeat is auscultated to input the data into the microprocessor; calculating the heart rate in the microprocessor using the input data; outputting the calculated heart rate to the display; and treating the neonatal patient based on where the calculated heart rate falls within the predetermined heartbeat thresholds. In one or more embodiments, the predetermined heartbeat thresholds may be set at ranges including less than 60 heartbeats per minute, between 60 and 100 heartbeats per minute and greater than 100 heartbeats per minute.

In still further embodiments of the invention, the present invention is directed to systems for providing real-time medical information that include an input device, the input device being actuated each time a heartbeat of a patient is auscultated to generate actuation data; a microprocessor coupled to the input device and receiving the actuation data from the input device, the microprocessor is programmed with predetermined heartbeat thresholds and calculates the number of times the input device is actuated using the input actuation data over a predetermined amount of time to generate a calculated heart rate; a display connected to the microprocessor that receives the calculated heart rate and outputs the calculated heart rate along with a unique identifier identifying whether the calculated heart rate is below, at or above any of the predetermined heartbeat thresholds; and treating the patient based on where the calculated heart rate falls within the predetermined heartbeat thresholds. In one or more embodiments, the predetermined heartbeat thresholds may be set at ranges including less than 60 heartbeats per minute, between 60 and 100 heartbeats per minute and greater than 100 heartbeats per minute.

In still other embodiments, the invention is directed to methods of treating a patient in need of medical treatment by providing the entire medical team with real-time medical information that include the use of a device for actuation that includes an input device; a microprocessor coupled to the input device, wherein the microprocessor is programmed with predetermined heartbeat thresholds and calculates the number of times the input device is actuated over a predetermined amount of time to generate a calculated heart rate; and a display connected to the microprocessor that receives the calculated heart rate and outputs the calculated heart rate along with a unique identifier identifying whether the calculated heart rate is below, at or above the predetermined heartbeat thresholds. The methods of treating a patient in need of medical treatment include actuating the input device each time a patient's heartbeat is auscultated; inputting the actuating data into the microprocessor; calculating the heart rate in the microprocessor using the input actuating data; displaying the calculated heart rate at the display; and treating the patient based on where the displayed heart rate falls within the predetermined heartbeat thresholds.

In accordance with the various embodiments of the invention described above and herein, the predetermined heartbeat thresholds may comprise predefined ranges of a newborn's heartbeats per minute. For instance, the predetermined threshold may be that of a newborn heartbeat, and detects whether the patient has less than 60 heartbeats per minute, between 61 and 119 heartbeats per minute and greater than 120 heartbeats per minute. In the various embodiments of the invention, the display may be activated once the input device has been actuated a predetermined number of times. For instance, the display may be activated once the input device has been actuated 1 or more times (e.g., 1, 2, 3, 4, 5, 6, 7, 8, 9, 10, 11, 12, 15 or more times). In certain embodiments the predetermined amount of time may be at least 0.1 seconds (e.g., it may be 0.1, 0.2, 0.3, 0.4, 0.5, 0.6, 0.7, 0.8, 0.9, 1, 2, 3, 4, 5, 6, 7, 8, 9, 10, 11, 12, 15 or more seconds). In accordance with the invention, the display may be updated with a rolling-average of heartbeats calculated at a select number of heartbeats (e.g., calculated every 1, 2, 3, 4, 5, 6, 7, 8, 9, 10, 11, 12, 15, etc. heartbeats). The display may be a numerical output that comprises the average heartbeats per minute. In certain embodiments, the display outputs a numerical output that comprises average heartbeats per minute, whereby the numerical output changes color depending on where the average heartbeats per minute fall within the predetermined heartbeat thresholds. In various embodiments of the invention, the display may output a different signal output that comprises average heartbeats per minute, whereby the different signal output changes depending on where the average heartbeats per minute fall within the predetermined heartbeat thresholds. In still other embodiments, the display may output a combination of a numerical output and a different signal output of average heartbeats per minute, whereby the numerical output and the different signal output change depending on where the average heartbeats per minute fall within the predetermined heartbeat thresholds. For instance, the display signal or color may change depending on whether a patient has less than 60 heartbeats per minute, between 60 and 100 heartbeats per minute, or greater than 100 heartbeats per minute. In one or more embodiments, the predetermined heartbeat thresholds may be set at whether a patient has less than 60 heartbeats per minute, between 60 and 100 heartbeats per minute or greater than 100 heartbeats per minute.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

Figure 1:
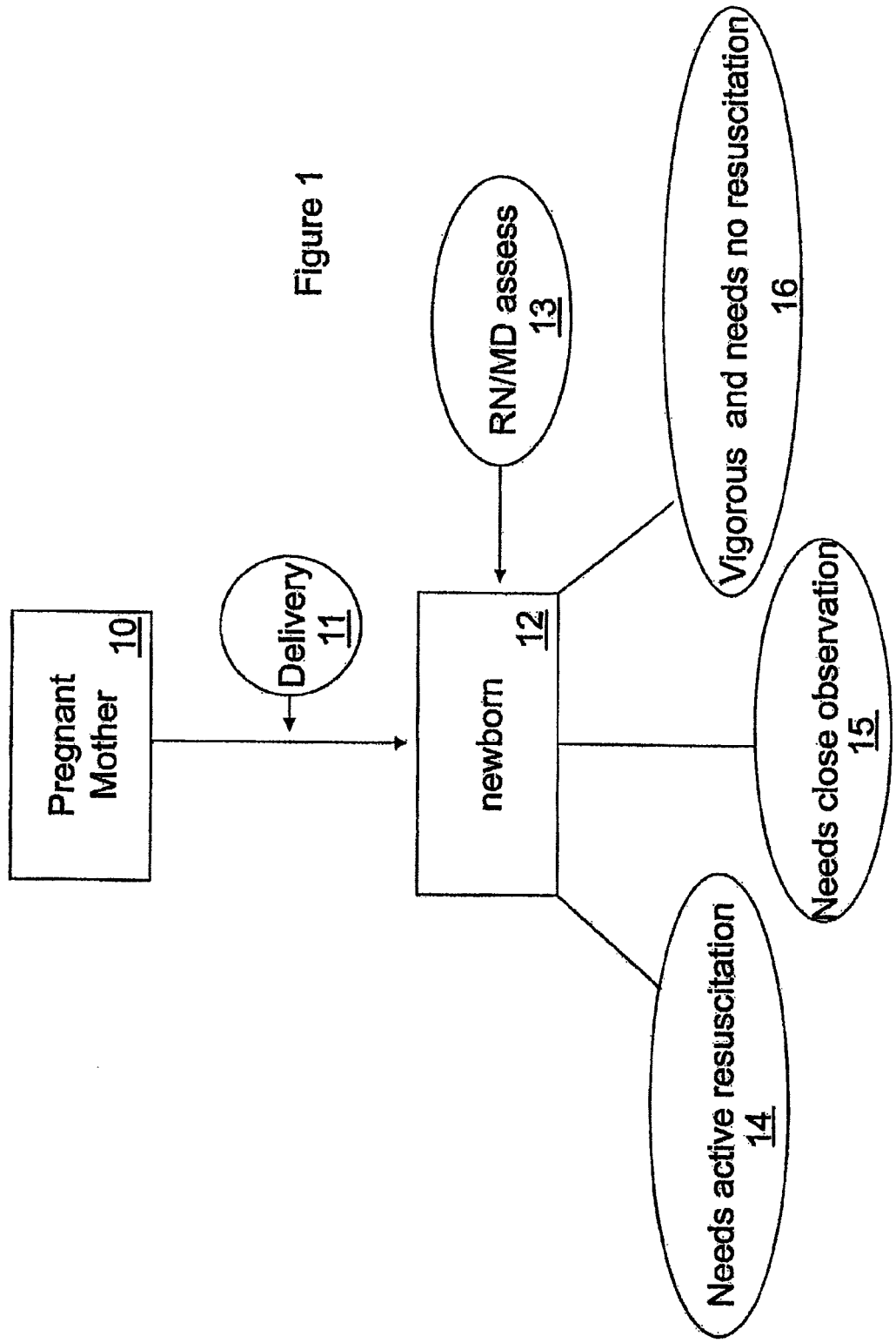
FIG. 1 is a flowchart summarizing the decision making for treatment of a newborn upon birth.

In describing the embodiment of the present invention, reference will be made herein to FIGS. 1-11 of the drawings in which like numerals refer to like features of the invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate an understanding of the present invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

More than half a century has passed since Virginia Apgar described the scoring system now used worldwide to evaluate the newborn in the first minutes of life. She described five (5) factors and scored each item from 0 to 2. These five (5) factors include color, cry, grimace, tone and heart rate, each being equally weighted. With the passage of time it became apparent that heart rate was the key element in evaluating the newborn in the first minutes of life. Heart rate is a key marker for cardiac output, which is primarily rate-driven in the newborn and young infant.

The first minutes of life are critical. Monitoring of a newborn's heart rate is essential and guides the established decision making algorithms for newborn resuscitation.

The normal heart rate in the newborn is 120 to 160 heartbeats per minute. The standard of care is for the medical professional to directly measure the patient's heart rate manually using, most often, a wristwatch and hearing heartbeats through a stethoscope, and after a certain amount of time, e.g., 10-20 seconds, mentally arriving at a possible calculation of a heart rate.

Resuscitation of the newborn is primarily driven by assessment of the heart rate by the newborn caretakers responsible for caring for a newborn in the delivery room, which may include one or more doctors in addition to nurses and other medical professionals and support staff. The methods used to assess heart rate immediately after birth include palpation of the newly cut umbilical cord or auscultation of the heartbeat with a stethoscope. The application of electrodes for EKG or sensor for a pulse oximeter takes time and must be verified manually before a determination is made that the electronic devices were connected properly and that their operation is accurately reflecting the condition of the patient. Typically, at least one to two minutes elapse, if not more, before the electronic monitors are attached in the delivery room after the birth of an infant requiring resuscitation. Furthermore, only the immediately attending medical professional has the immediate heart rate information, which is often delivered in a high tension, high stakes environment by speaking or verbally announcing the manually obtained estimate of heart rate (i.e., the manual, mentally calculated heart rate) to other medical team members at a specific time, or time intervals. Even after leads for EKG or pulse oximeter are applied and a signal obtained, the validity of the heart rate has to be double checked by auscultation with a stethoscope. In situations where cardiac output is low and heart rate is low, the electronic devices for monitoring heart rate are often problematic and repeated auscultation is required.

Furthermore, difficulties exist in manually calculating heart rate and providing feedback to other members of the newborn resuscitation team with auscultation of the heart rate. Either a stopwatch or a second-hand on a wall clock is used, and typically a six second elapse time period is used to calculate the newborn heart rate which is then multiplied by a factor of 10 to obtain the manually estimated heart rate. This number is communicated to the other team members responsible for the resuscitation. During the intense atmosphere of a newborn resuscitation, these activities are often challenging, even to those individuals experienced at such practices. When inexperienced individuals are responsible the problems are magnified. Additionally, these manually obtained heart rates are at best an estimate, and are rarely accurate.

The algorithm for newborn resuscitation is guided by heart rate. The newborn with a heart rate over 100 heartbeats per minute and with the rate rising requires minimal assistance. However, an infant with a heart rate less than 100 heartbeats per minute, ventilation assistance is required for such infant. Those with heart rates less than 60 heartbeats per minute, and are not responding to ventilation after 30 seconds, require external cardiac massage to support cardiac output. Repeated evaluation of heart rate is then required until all interventions prescribed by standard resuscitation algorithms have been carried out.

In one or more embodiments, the present invention provides devices, systems and methods that immediately count a newly born infant's heart rate and share such heart rate information in real-time to an entire medical team so that the entire team has an immediate assessment of the heartbeat without adding additional noise and/or confusion in the treatment area. These counts and shared results may be shared within as few as possible heartbeats including, but not limited to, in as few as 3, 4, 5, 6, 10, 12, 15, 20, or 25, etc. heartbeats.

In accordance with one or more embodiments of the invention, a caretaker may continue to auscultate the heartbeat, which continues to be an integral part of newborn resuscitation and evaluation in a delivery room and NICU. The embodiments of the invention allow the auscultator to press a small electronic radio transmitter attached to the stethoscope in sync with the auscultated heartbeat. The radio signal generated may be ultimately transmitted to a monitor and displayed as a visual and audible heart rate.

In accordance with one or more embodiments, the invention includes a unique set of instructions (e.g., a unique program) that enables the monitor to alert caretakers of critical heart rate ranges including, but not limited to, critical heart rates of 60 or below per minute, heart rates ranging from 60 to 100 per minute, and heart rates over 100 per minute. These rates may be uniquely displayed (e.g., color coded) to alert the caretakers to the recommended interventions needed at these critical heart rates. For example, 60 or less heartbeats per minute may be displayed and color coded in a first color (e.g., red), while 60 to 100 heartbeats per minute may be color coded in a second color (e.g., amber), and still further, heart rates over 100 per minute may be color coded in a third color (e.g., green). The monitors and devices of the invention may also be enabled with auditory transmitters to verbally/auditorily alerts or reminders to assist the team in the recommended next steps in resuscitation.

Furthermore, the embodiments of the invention may also keep and export a record of time and heart rate over time that may be reviewed after the resuscitation is complete. The data may be used for a permanent record of the time sequence of heart rates that have been auscultated, or even for teaching medical professionals in controlled environments prior to actual use of the invention on a patient.

The various embodiments of the invention eliminate the difficulties in counting heart rate when the challenges of difficult auscultation and estimating heart rate described above cannot be overstated. For the first time, a display that is easily viewed and heard by the medical team will be available before electronic signals are available. In so doing, the present invention facilitates timely interventions for successful resuscitation of the newborn.

Referring now to the drawings, FIG. 1 is a flowchart that summarizes a decision making process for treatment of a newborn upon birth. When a pregnant mother 10 approaches the time for delivery 11, the medical team will prepare for the arrival of the newborn 12. The registered nurse and/or medical doctor 13 assess the condition of the newborn 12 and make a determination whether the newborn 12 needs active resuscitation 14, needs close observation 15, or is vigorous and as such needs no resuscitation 16.

Figure 2:
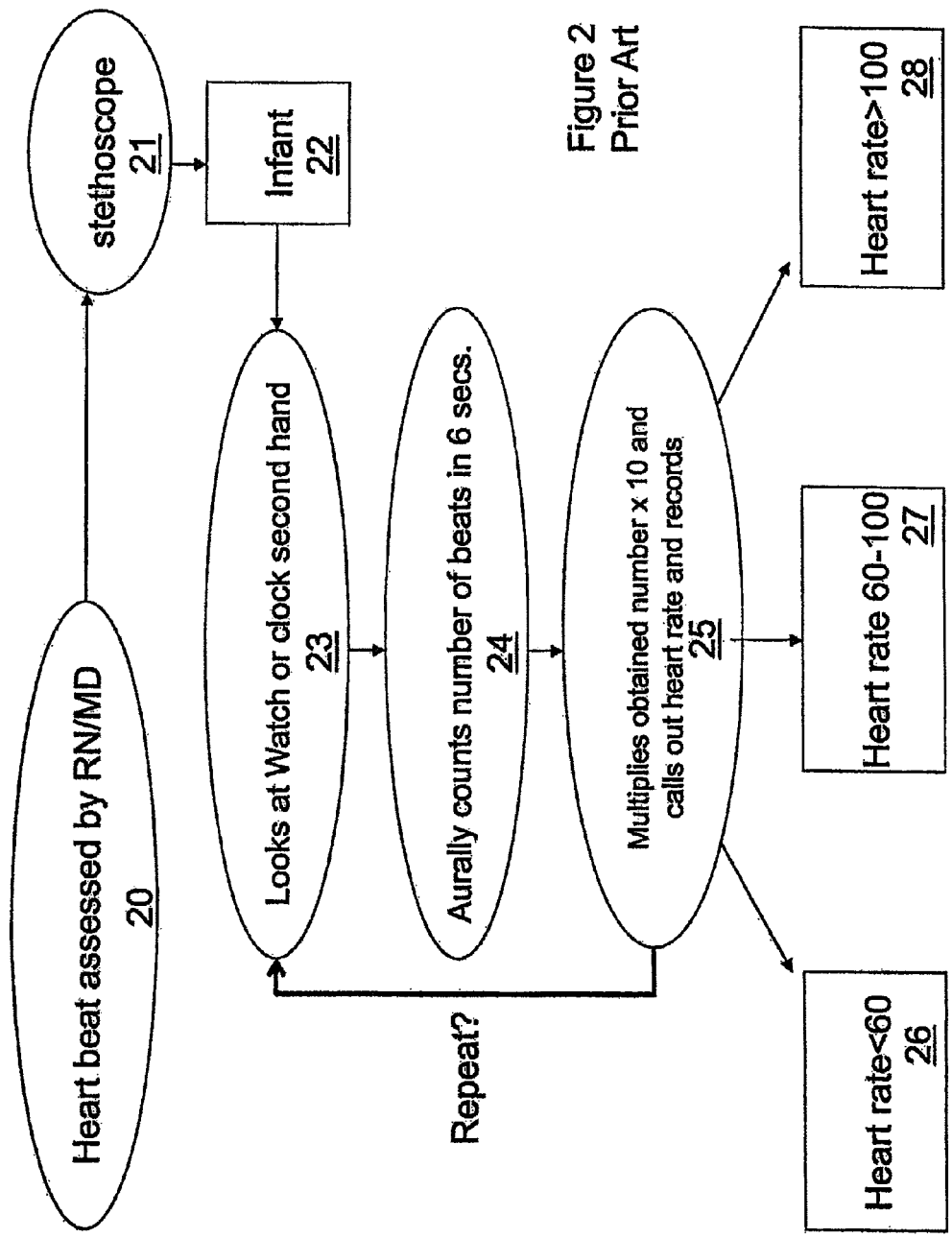
FIG. 2 is a flowchart summarizing the decision making for the on-going evaluation of a newborn upon the determination that the patient may be under distress.

FIG. 2 illustrates a flowchart of the known decision making process for the on-going evaluation of a newborn upon the determination that the patient may be under distress. In step 20, the heartbeat is assessed by an RN or MD using a stethoscope 21 on the infant 22, while the RN/MD looks at a clock or a watch 23, and counts the second hand 24. In step 24, the RN or MD aurally counts the number of heartbeats in approximately 6 seconds, and then mentally calculates the heartbeat by multiplying the number of heartbeats counted in the approximately 6 seconds by a factor of 10, and calls out the heart rate to the other medical team personnel. This calculated heartbeat may, or may not, be recorded 25. Based on this initial determination, or one or more subsequent determinations, the RN/MD determines if the infant has a heart rate of less than 60 (26), between 60 and 100 (27), or greater than 100 (28) heartbeats per minute.

Figure 3:
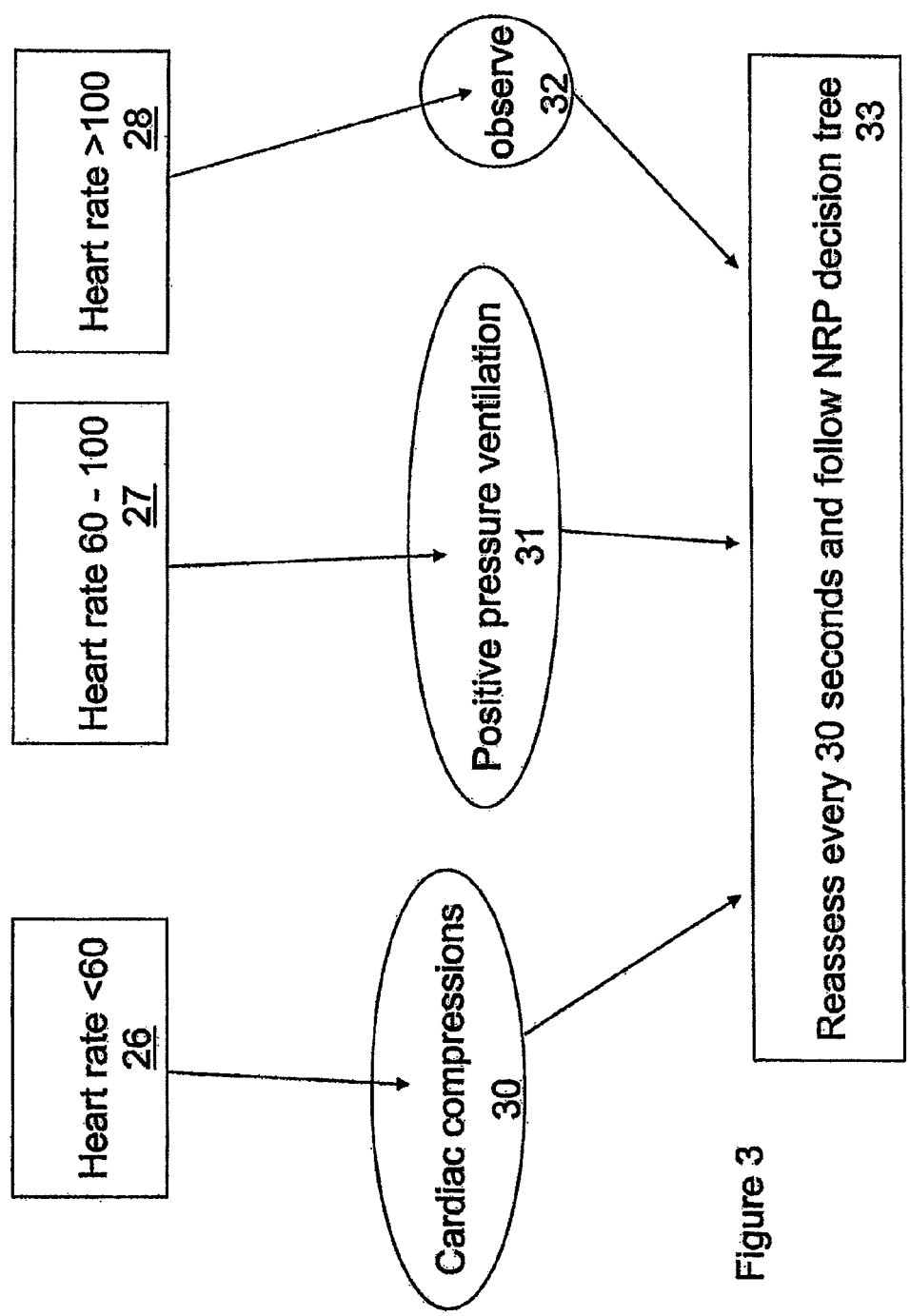
FIG. 3 is a flowchart summarizing the decision making for the treatment of a newborn upon a determination that the patient may be under distress.

FIG. 3 is a flowchart that summarizes the decision making process for the treatment of a newborn upon a determination that such newborn may be under distress. Depending on whether the infant had a heart rate of less than 60 (26), between 60 and 100 (27), or greater than 100 (28) heartbeats per minute, the medical team may then initiate cardiac compressions 30, provide positive pressure ventilation 31, or continue to observe 32 the infant, respectively. The condition of the infant is reassessed 33 every 30 seconds and the Neonatal Resuscitation Protocol (NRP) is then followed. In the prior art, each of these steps is manually conducted by the medical team based on ad hoc timing depending on the circumstances surrounding the infant without any indicator of timing.

Figure 4:
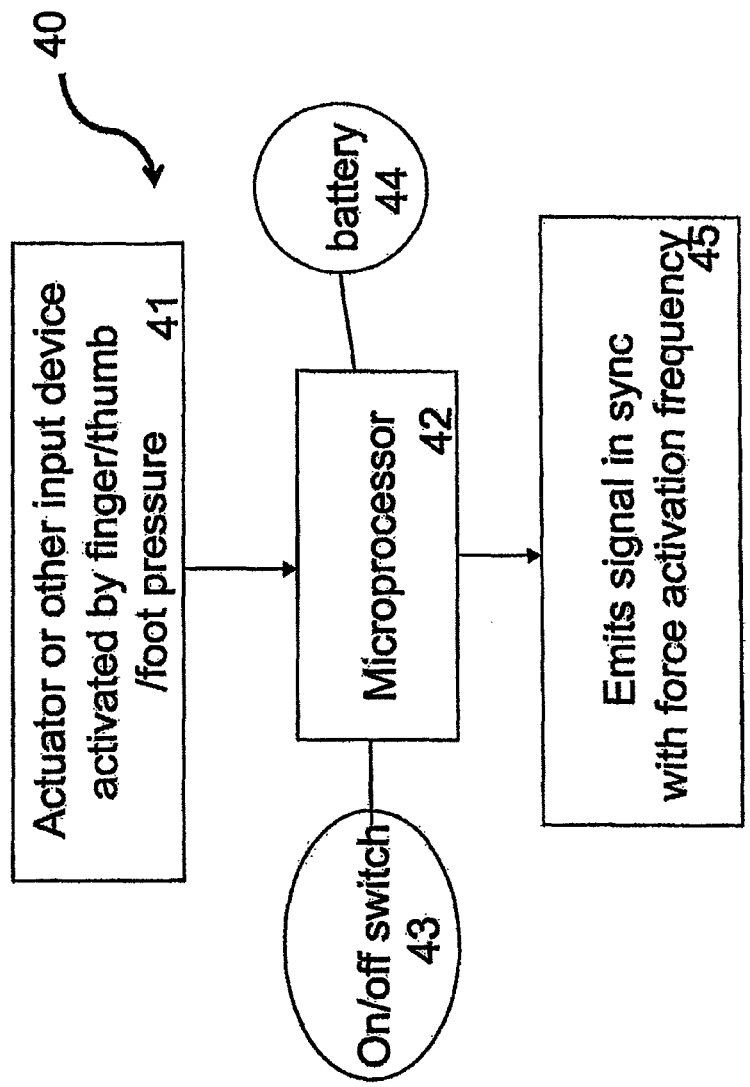
FIG. 4 shows one or more embodiments of the devices of the present invention.

FIG. 4 shows components of one or more devices 40 of the invention. An actuator 41 (or other input device such as a mechanical, electrical, magnetic, infrared, microwave or other device that detects motion) is positioned such that a user that is auscultating the patient can input a heartbeat event every time such person hears a heartbeat by triggering the actuator 41 with a thumb, finger, foot or other manual input. The actuator 41 is connected to a microprocessor 42 that is in communication with an off/switch 43 and/or a battery 44 that powers the microprocessor 42. The microprocessor 42 receives the output from the actuator 41. It has a set of instructions therein for determining the heartbeats per minute based on the time that has elapsed. In so doing, the microprocessor 42 uses the data input from the actuator 41 and calculates a time interval between inputs by comparing to a timer or clock with as few as two output signals from the actuator to determine the number of heartbeats per minute. The microprocessor 42 then sends a output signal that indicates visually and/or aurally each heartbeat, the number of heartbeats per minute, an indicator of the time that has elapsed (e.g., every 30 seconds), a graph that tracks the on-going measurement of the heart rate, and a display that changes color, shape, vector or other indication of the heart rate of the patient.

Figure 5:
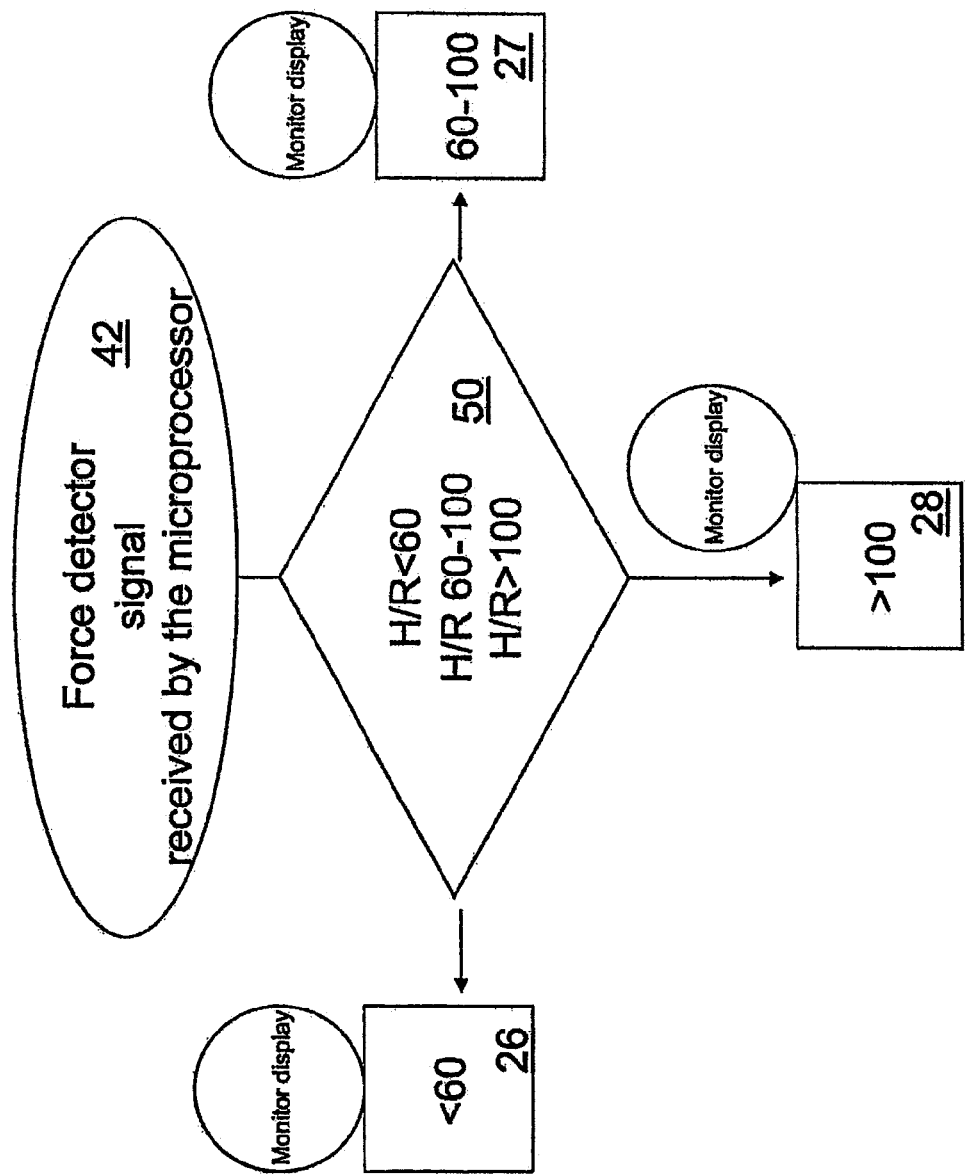
FIG. 5 is a flowchart of the data processing and processor output of various embodiments of the invention.

FIG. 5 shows a flowchart of the data processing and processor output in accordance with one or more embodiments of the invention using, for instance, a device 40 of the invention as shown in FIG. 4. The microprocessor 42 calculates the heart rate 50 using the data input from the actuator 41, and outputs such calculated heart rate at the display monitor. The display monitor shows the output heart rate data using unique indicator(s) or identifier(s), such as, the actual numerical heart rate, a color indicator (e.g., red, yellow/orange and green), or a combination of the two in outputs, thereby notifying all medical personnel attending to the infant whether such infant has a heart rate of less than 60 per minute (26), between 60 and 100 per minute (27, or greater than 100 (28) heartbeats per minute.

Figure 6:
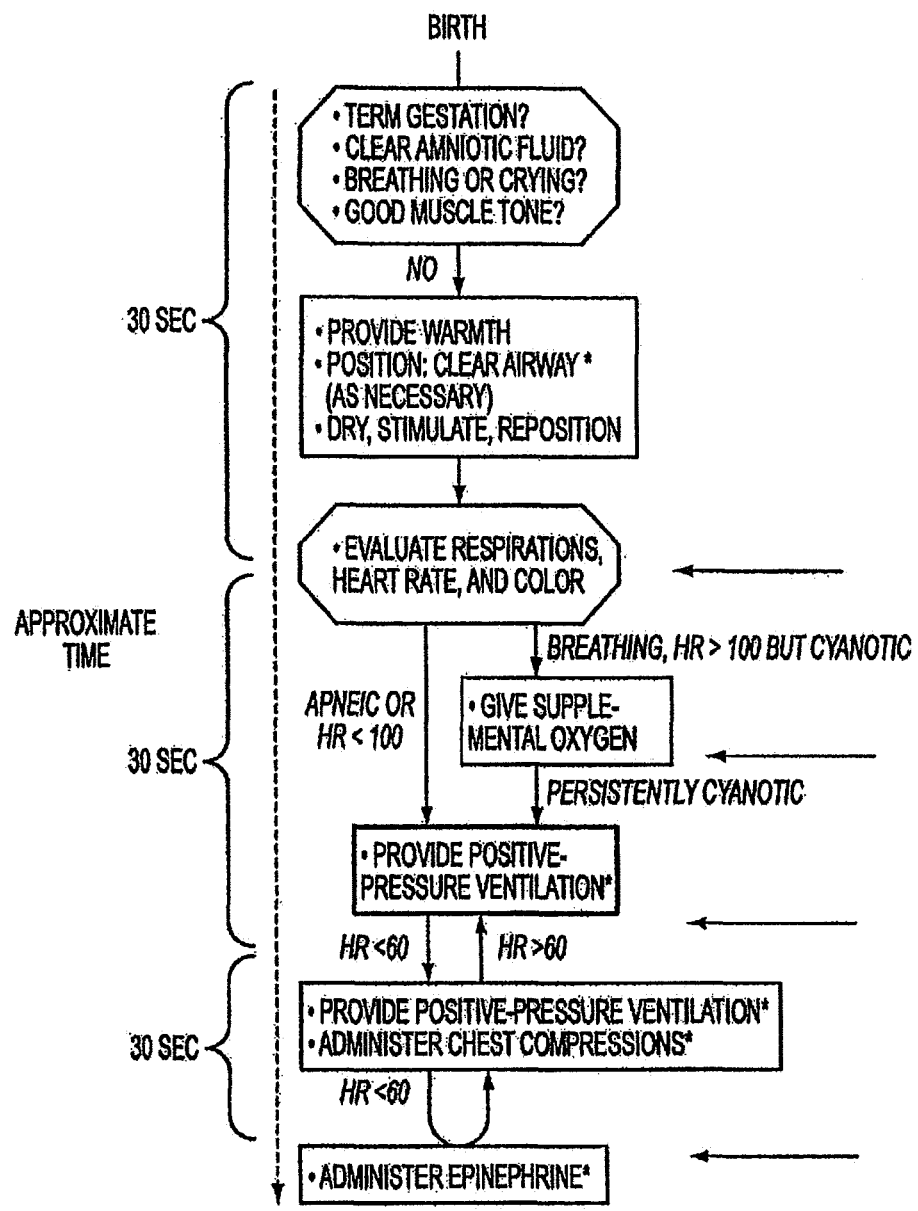
FIG. 6 is a NRP/AAP Resuscitation Flow Chart demonstrating timelines involved in decision-making showing times at which use and/or implementation of the present invention are beneficial.

FIG. 6 is a standard NRP/AAP Resuscitation Flow Chart that demonstrates the timelines involved in decision-making and represents the times during which various devices, systems and methods of the present invention are critical. The different arrows show the times at which the various embodiments of the invention may be implemented to allow the medical team to make determinations that heretofore were based on mental calculations, and for which, the present invention allows for the first time to meet the need of the medical team to provide accurate data on the heart rate of the infant.

Figure 7A:
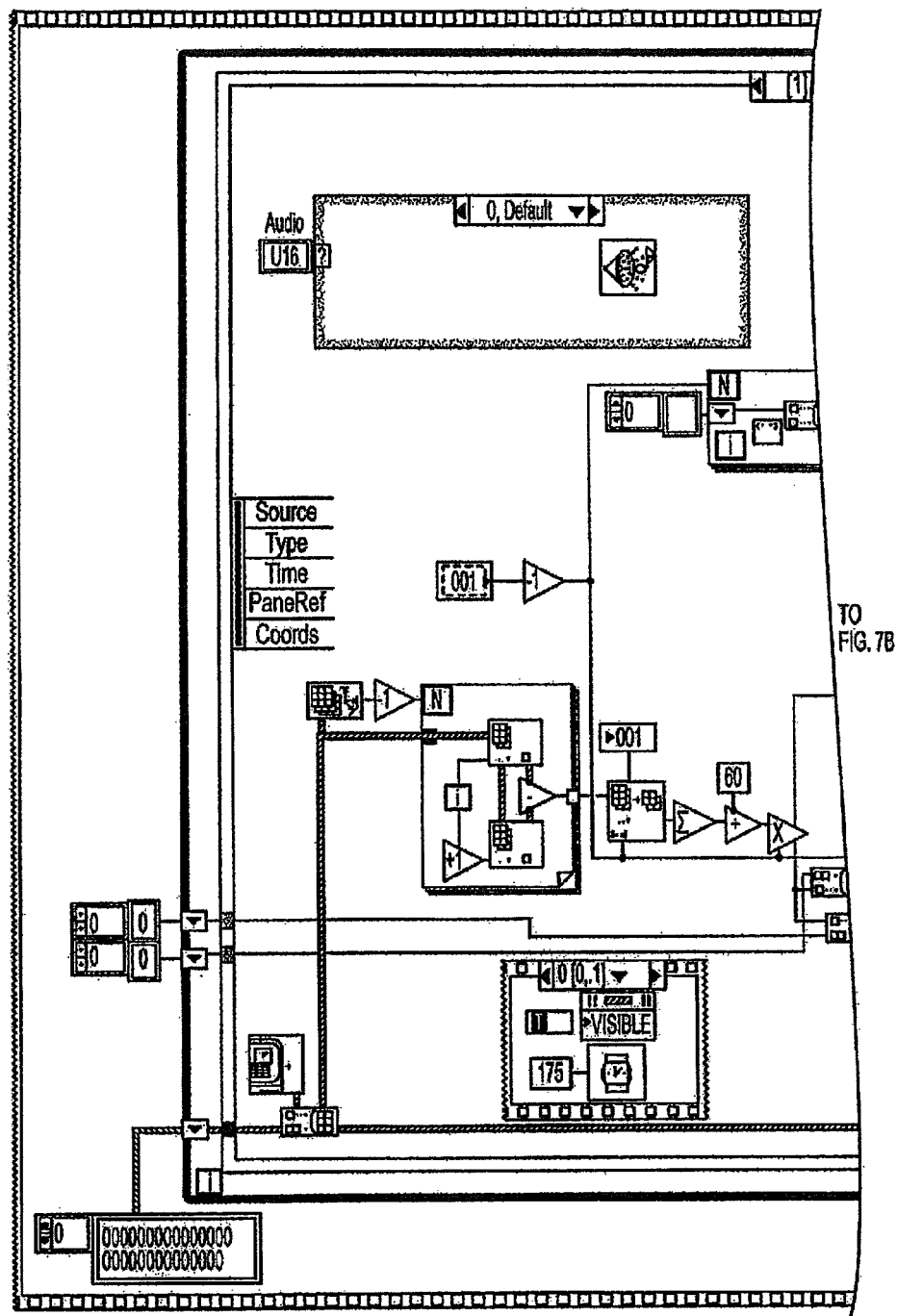
FIGS. 7A-C sequentially illustrate a flowchart of one or more processor implementations that may be used as part of the data processing of various embodiments of the invention.
Figure 7B:
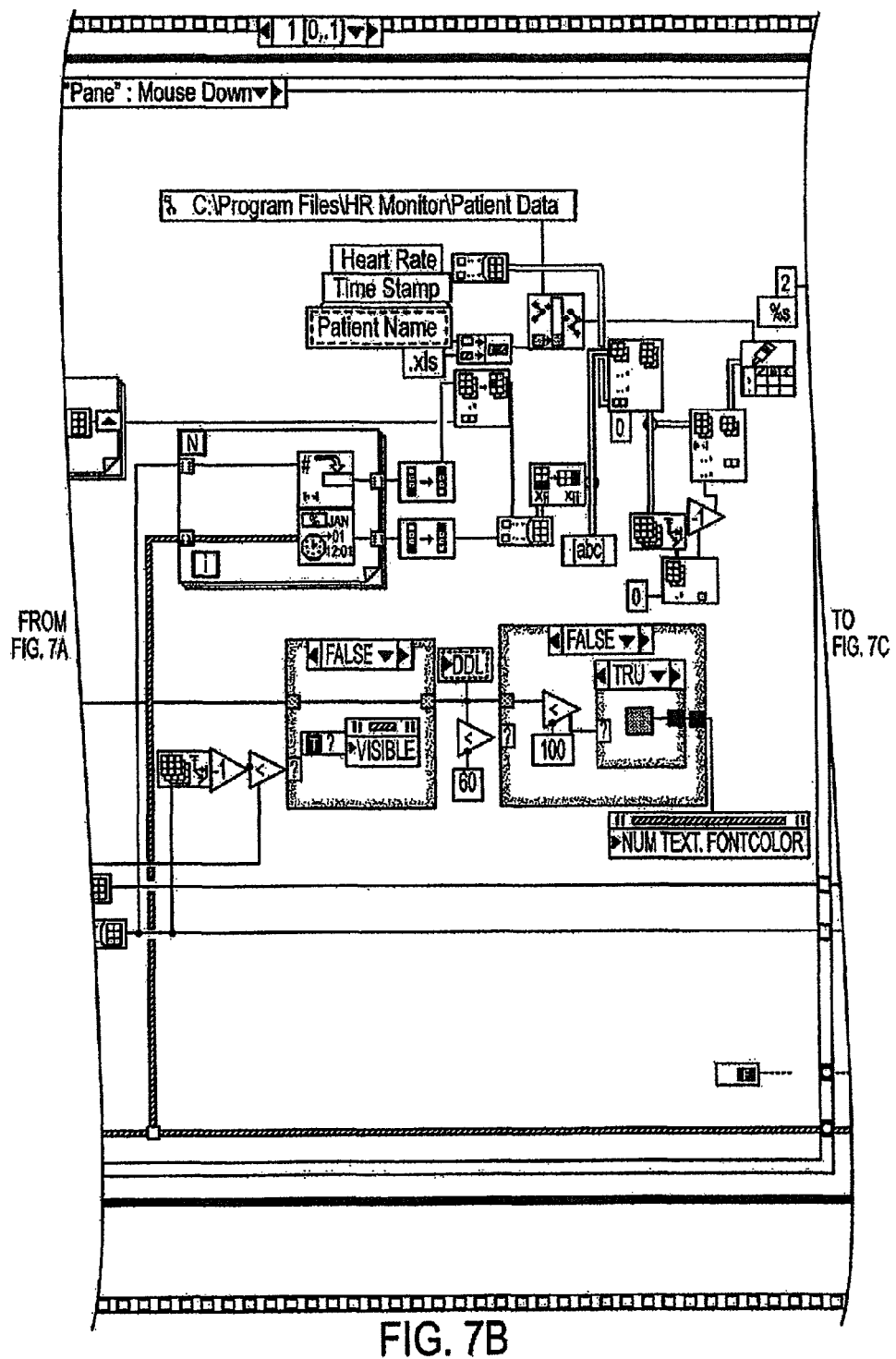
Figure 7C:
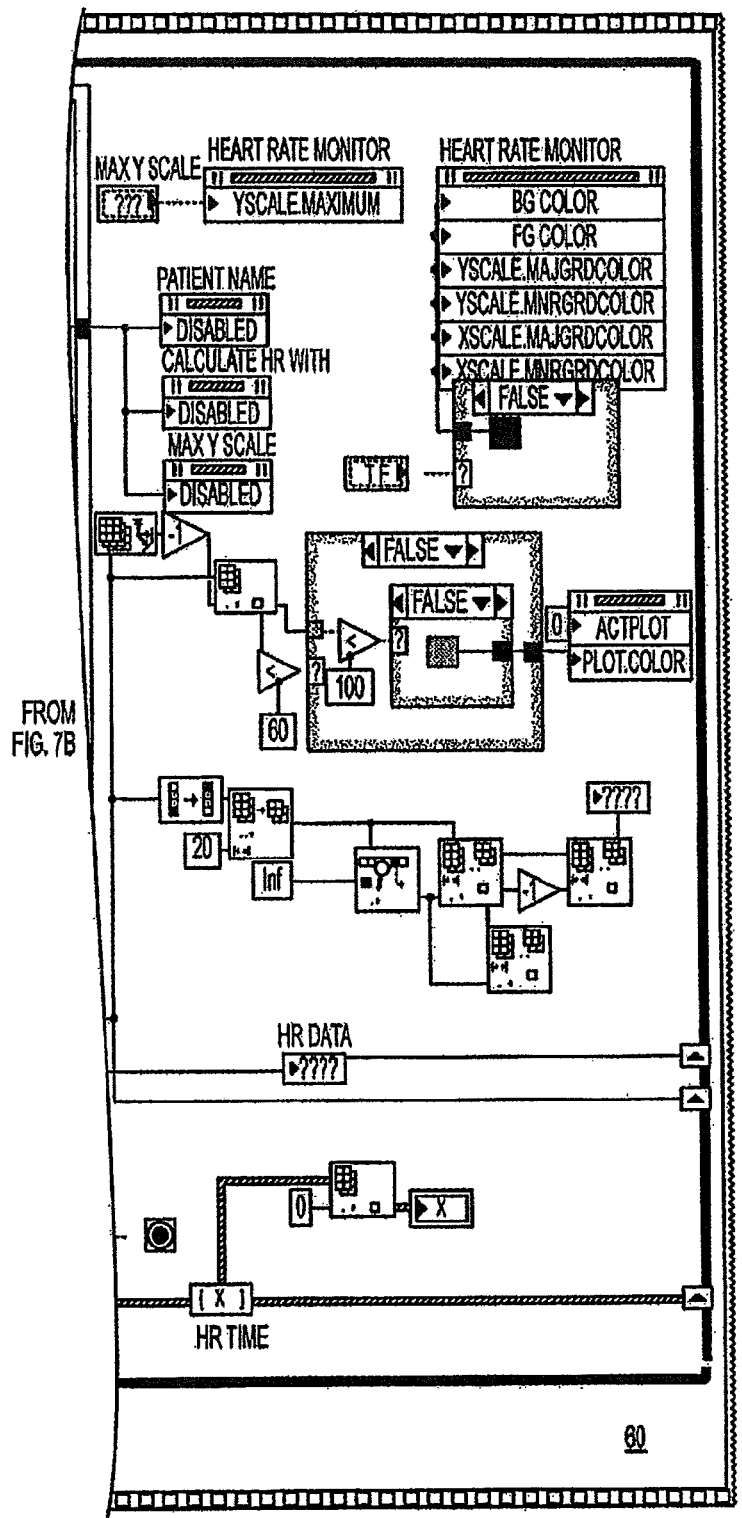
Figure 8:
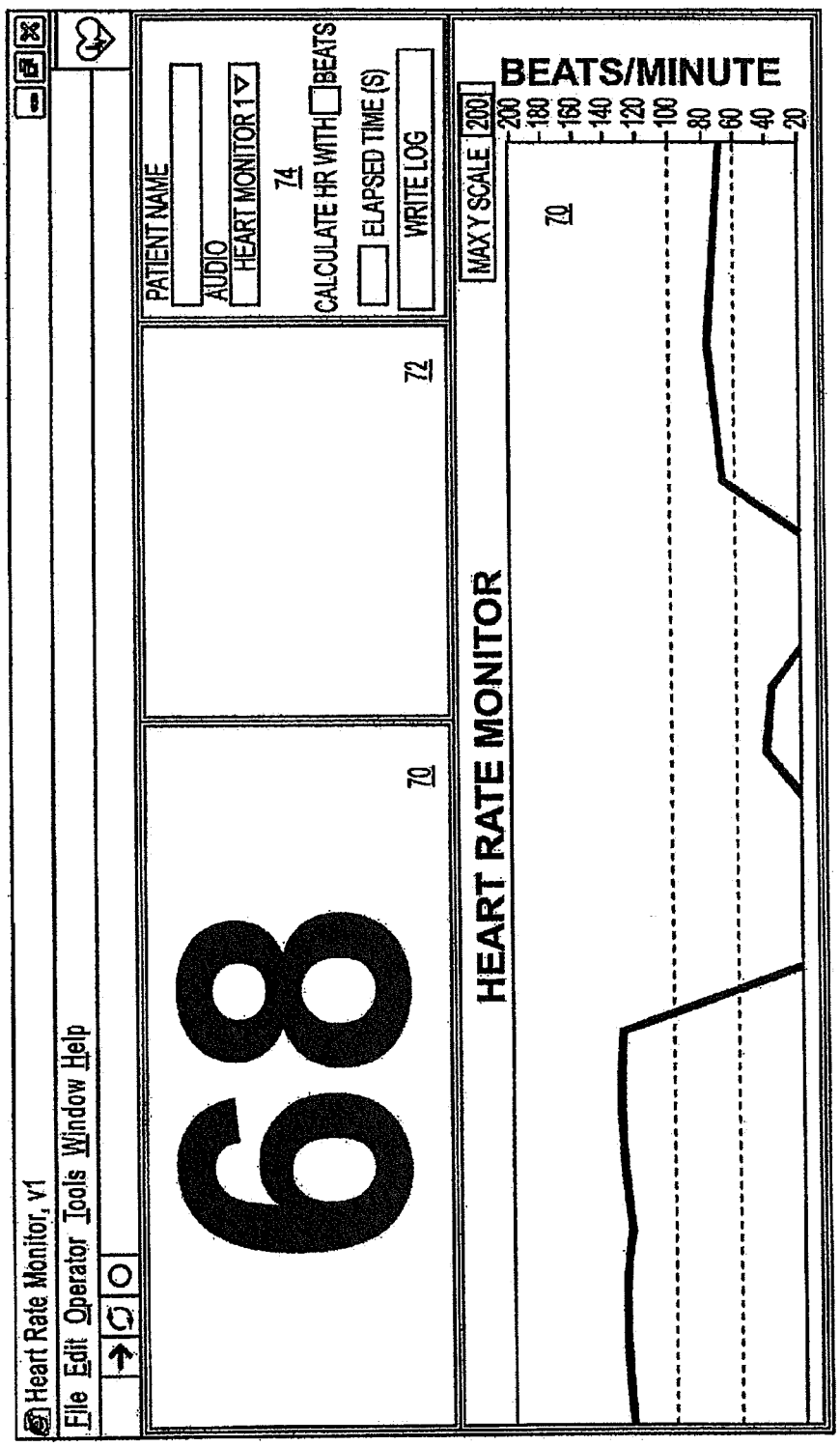
FIGS. 8, 9, 10 and 11 show outputs of data generated in accordance with various embodiments of the invention.
Figure 9:
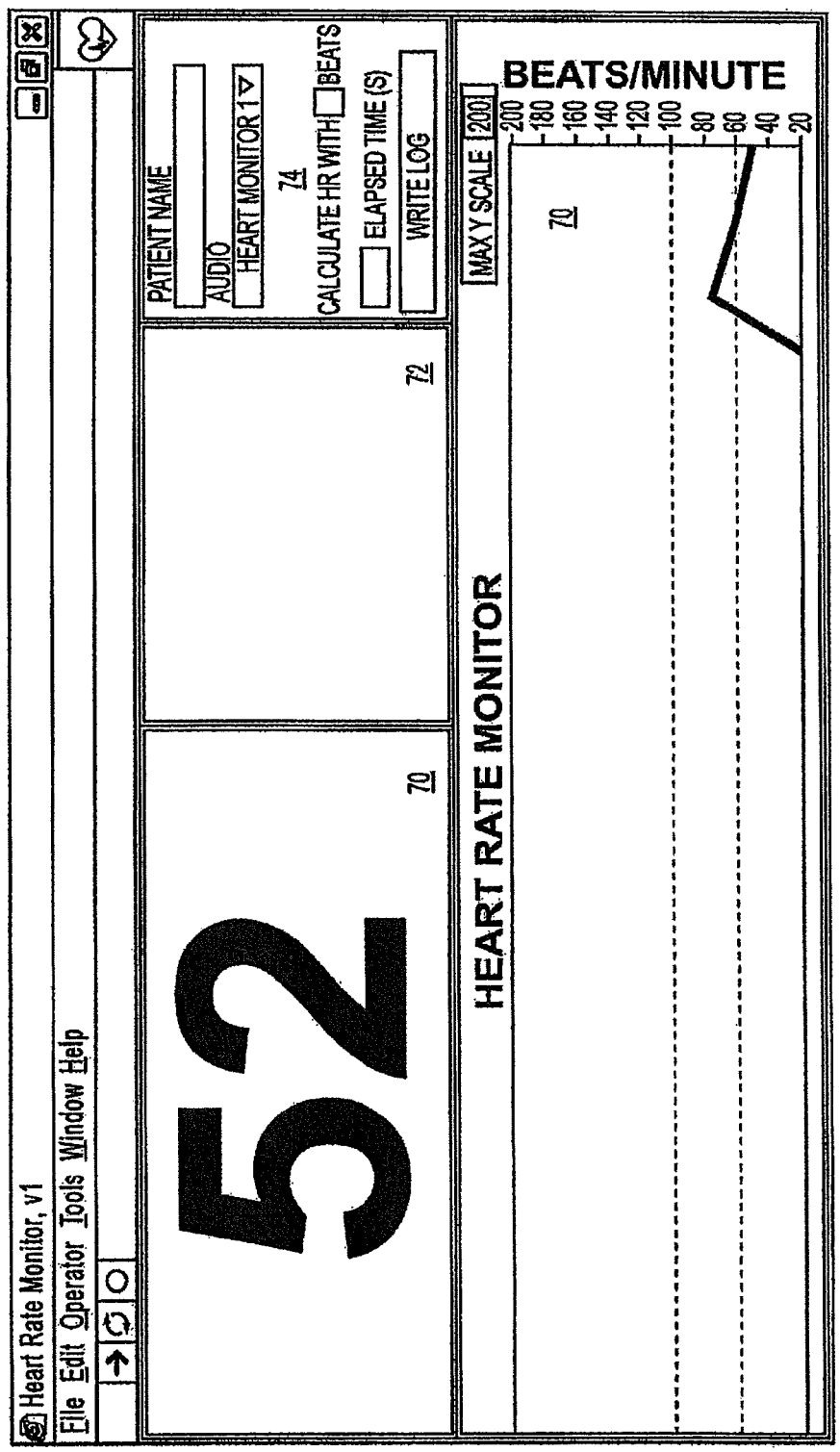

FIGS. 7A-B illustrate an example of a flowchart of one or more processor implementations of the invention that may be used as part of the data processing of the invention. The Heart Rate Monitor program was designed using LabView, which is a graphical programming environment. LabView is a coding product of National Instruments (Austin, Tex.). The skilled artisan will recognize that other coding environments and/or computer languages may be used to provide the functionality of the various embodiments of the present invention.

In accordance with the invention, one or more embodiments of the invention may include a set of instructions (e.g., a program) contained in a stacked sequence structure consisting of two, or more, frames. The first frame initializes the graph and the numeric display arrays with no data. This frame also loads the picture (.jpg) of the heart. The second frame (64) of the stacked sequence structure contains a while loop. A while loop repeats a subdiagram inside it until forced to stop either by a conditional terminal, in this case by selecting the "Write Log" button, or by manually aborting the program by selecting a stop sign. The while loop has three (3) shift registers; one for the heart rate numerical display, one for the graphical display, and one for the time stamp that is created with each mouse click. In the while loop there is an event structure, which has one or more subdiagrams, or event cases, exactly one of which executes when the structure executes. The event structure waits until an event happens then executes the appropriate case to handle that event. There are three frames in the event structure, frame 0, 1, and 2. Event 0 is the timeout frame. No code is present here. A mouse click, or more specifically the mouse down position, activates frame 1 of the event structure. After the mouse click, which activates the code in frame 1, the event structure advances to frame 2. If the "Write Log" button is pressed the program ends and an Excel (.xls) file may be written with the patient's name (default value: John Doe) with an ".xls" extension and be place in a directory (e.g., directory—C:\Program Files\HR Monitor\Patient Data). If the "Write Log" button is not pressed, the shift registers may be used to carry over the values from the last iteration to the next iteration, thereby building up the arrays of data for the time stamps added from the mouse down position and the heart rate calculated from these time stamp intervals.

In these embodiments, it is in the event structure in frame 1 when the mouse is in the down position where the heart rate calculation is generated and displayed. An array consisting of a time stamp is created and initialized. Each mouse click adds that time stamp to the array. The interval between each mouse click is calculated. The user selects the number of heartbeats to use for the heart rate calculation. The default value is three. This number is then decremented by 1. This is the number of most recent intervals that is summed together, then divided into 60 seconds, and then multiplied by that decremented number to give the heart rate. The number of heartbeats selected may not be calculated correctly until that number is reached and therefore the numeric and graphical display may not be visible until such number is reached. These numbers may not be present in the .xls file.

In this event structure frame, the audio files are loaded. The selected audio activates with each mouse click as well as the .jpg file. The last heart rate value is taken and the color of the numeric and graphical heart rate is selected (e.g., red if the heart rate is under 60 heartbeats per minute, orange if between 60 and 99 heartbeats per minute, and green if 100 or above heartbeats per minute).

While not meant to be limiting, the following is an example of one or more embodiments of the present invention. In accordance with various embodiments, the set of instructions for implementing the methods and apparatus of the invention may be initiated by double clicking on a Heart Rate Monitor executable file (Heart Rate Monitor.exe). In this example, the program begins as the "Elapsed Time (s)" box begins to increment in seconds. This value is not used for calculation purposes. The Tab key allows the user to navigate from control to control. Tab order may be set to:

1. Patient Name—input patient name that may be used to name a data log file (.xls). Default value is John Doe.

2. Audio—a drop down menu with options for a computer beep, silent, or 2 options for .wav files. Default value is Heart Monitor 1.wav 3. Calculate HR with # of heartbeats—The number selected in this box may use the time between that number of last mouse clicks to calculate the current heart rate. The time between the last number of mouse clicks are added up, then divided by 60, and finally multiplied by the number selected minus one to result in current heart rate. When the program begins, a numeric heart rate may not be shown until that number of mouse clicks selected has been reached in order to maintain accuracy. If at any time during the program execution the program remains idle, the heartbeat accuracy may not be achieved until that selected number of mouse clicks is achieved again. Recommended and default value here is 3.

4. Select the maximum value for the Y-scale—This allows the user to change the y-scale maximum value on the graph, which represents heartbeats per minute. The default value is set at 200.

5. Write to log file—Upon completion of use, selecting this button uses the name in the Patient Name box to create a Microsoft Excel (Name.xls) file located in C:\Program Files\HR Monitor\Patient Data. The table below is an example.

| Heart Rate | Time Stamp |
|---|---|
|  | 3/24/2010 14:35 |
|  | 3/24/2010 14:35 |
|  | 3/24/2010 14:35 |
| 55 | 3/24/2010 14:35 |
| 55 | 3/24/2010 14:35 |
| 56 | 3/24/2010 14:35 |
| 51 | 3/24/2010 14:35 |
| 53 | 3/24/2010 14:35 |
| 57 | 3/24/2010 14:35 |
| 70 | 3/24/2010 14:35 |
| 83 | 3/24/2010 14:35 |
| 92 | 3/24/2010 14:35 |
| 101 | 3/24/2010 14:35 |
| 91 | 3/24/2010 14:35 |
| 80 | 3/24/2010 14:35 |

-continued

| Heart Rate | Time Stamp |
|---|---|
| 76 | 3/24/2010 14:35 |
| 80 | 3/24/2010 14:35 |

In the various embodiments of the invention it is possible in Excel to further expand the Time Stamp to include seconds, if desired, through the Format→Cells→Number-→Custom menu. Under Type, select "m/d/yyyy h:mm" option and manually append ":ss". Then select OK. Selecting the Write Log button may not allow any further data collection. The program may have to be stopped and run again.

Selecting the Tab key again brings the User back to Patient Name. In order to input a patient's name, press the Tab key once after the program is running. Do not use the mouse while the program is running in order to navigate through options. The mouse is strictly for heart rate input and selecting the Write Log button. The program should be started after opening the executable file although it may be stopped at any time by pressing a RED Stop Sign located in the top left of the window. Selecting the Arrow to it's left can restart the program. Upon completion of entering the patient's name, select the Tab key again, and then select the preferred Audio setting. Select the Tab key again, and then select the number of consecutive heartbeats desired to calculate current heart rate. If any of the default values are satisfactory, the Tab key may continue to be used to circulate through the options.

Heart rate calculation will begin as soon as a mouse click is initiated INSIDE the program window. The Patient Name box and Calculate HR with # of heartbeats may be grayed out and not reset until termination of the program. It is preferred that the mouse clicks coincide with the heartbeats as closely as possible for accuracy. The current rate may be shown numerically in the top left corner of the program window. A picture of a heart (.jpg) acts as a visual aid, and appears with each click of the mouse, as well as the audio preference (if silent mode is not selected). The displayed heart rate is color-coded based upon the current heart rate as well as the graph on the lower half of the program window. For instance, the color codes may be:

Heart Rate under 60 heartbeats per minute=RED
Heart Rate between 60 and under 100 heartbeats per minute=ORANGE/YELLOW
Heart Rate 100 heartbeats per minute and over=GREEN The graph, which may be located on a bottom half of the program window, may hold the last registered heartbeats, e.g., a maximum of the last 20 heartbeats. The most current heart rate reading appears along the y-scale located on the right side of the graph, which reads in chronological order from left to right. Data is stored, and as such, is not lost if such data is not displayed on the graph. Preferable, all heartbeat data is stored in memory and is written to a data log file.

Figure 10:
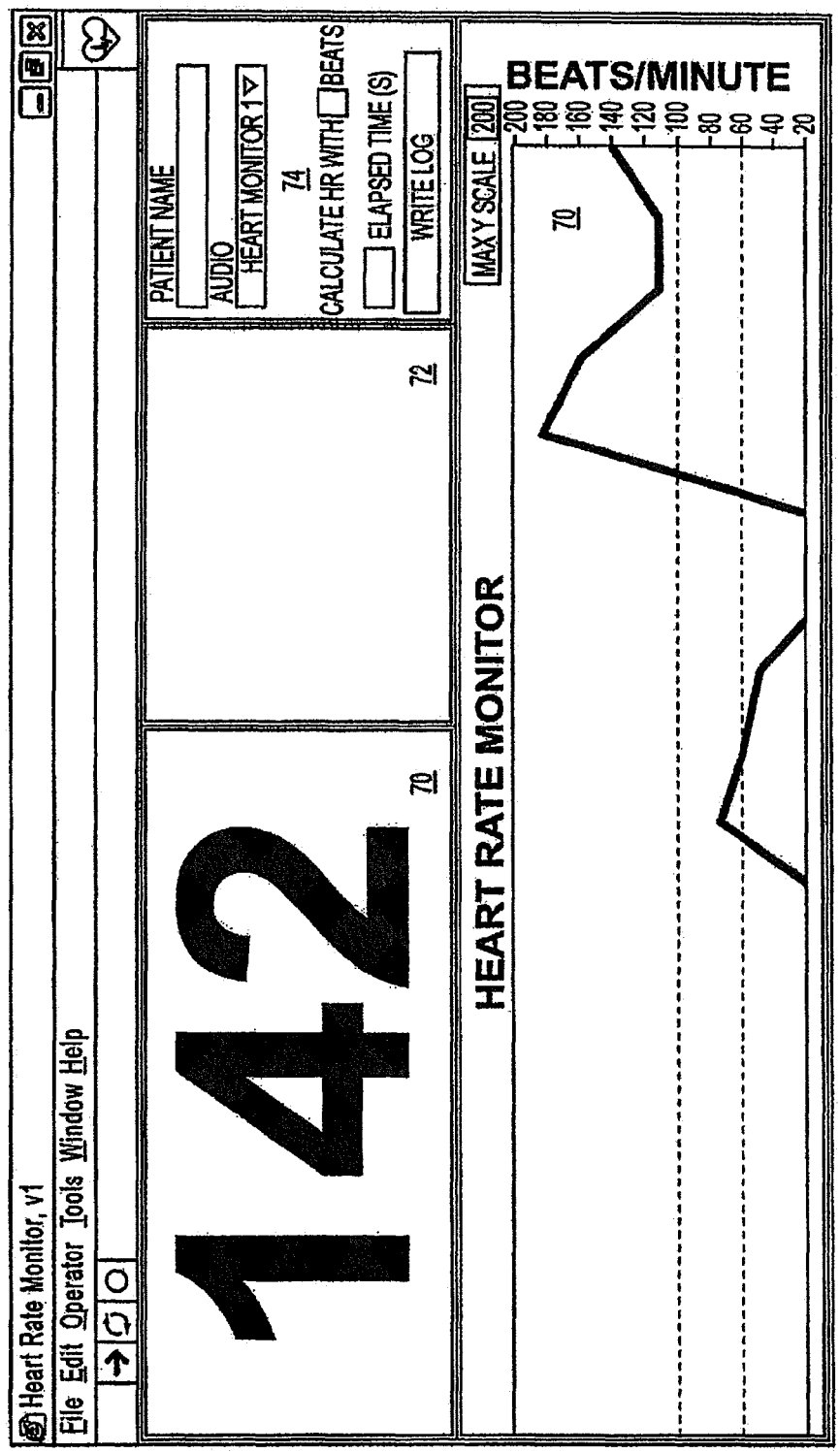

FIGS. 8-11 illustrate examples of Heart Rate Monitors in accordance with the various embodiments of the invention. The figures show screen shots of such Heart Rate Monitors displaying outputs of the invention. These outputs display various numerical heart rates 70, including, but not limited to a display of 68 heartbeats per minute (FIG. 8), a display of 52 heartbeats per minute (FIG. 9), and a display of 142 heartbeats per minute (FIG. 10). Again, these displayed heartbeats may be color coded, e.g., the 68 of FIG. 8 may be displayed in orange, the 52 of FIG. 9 may be displayed in red, and the 142 of FIG. 10 may be displayed in green.

Figure 11:
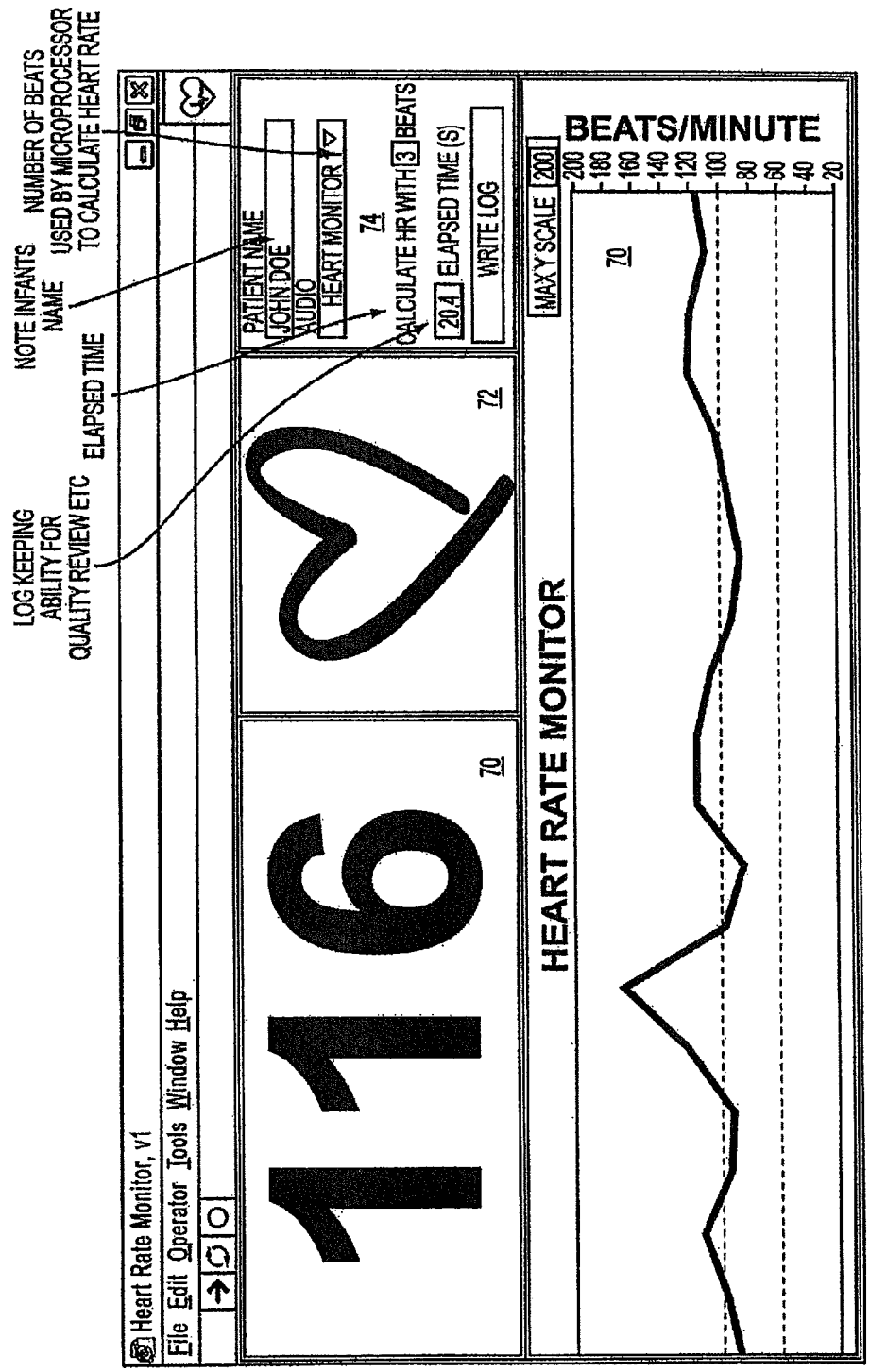

FIG. 11 shows that each time a user inputs a heartbeat, a heart 72, or like indicator, is depicted adjacent the numerical heart rate indicator. Below the heart rate 70, is a graph 74 that shows the measured number of heartbeats in real-time. This graph may also change color as the heart rate changes over time. Patient, and optionally user information, is depicted to the right of the heart 72 in box 76. FIG. 11 also shows further details of screen displays in accordance with the invention, including, but not limited to, displaying the time elapsed, a variable input parameter that is used to calculate the number of heartbeats used to calculate the heart rate (in this case, depicted as three heartbeats per calculation), whether an audio output is provided, patient information, and whether to write a log of the calculations.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon. Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in base band or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the end-user's computing device (such as, a computer), partly on the end-user's computing device, as a stand-alone software package, partly on the end-user's computing device and partly on a remote computing device or entirely on the remote computing device or server. In the latter scenario, the remote computing device may be connected to the end-user's computing device through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computing device (such as, a computer), special purpose computing device, or other programmable data processing apparatus to produce a machine, such that the instructions, which execute via the processor of the computing device or other programmable data processing apparatus, create means for implementing the functions/acts specified in the flowchart and/or block diagram block or blocks. These computer program instructions may also be stored in a computer readable medium that can direct a computing device, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computing device (such as, a computer), other programmable apparatus or other devices to produce a computer implemented process such that the instructions which execute on the computer or other programmable apparatus provide processes for implementing the functions/acts specified in the flowchart and/or block diagram block or blocks.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

Thus, having described the invention, what is claimed is:

1. A device for reporting a heart rate comprising:
   an input device that receives a signal each time a heartbeat of a patient is detected, the input device being actuated by an end-user each time the patient's heartbeat is auscultated;
   a microprocessor coupled to the input device, wherein the microprocessor is programmed with one or more predetermined heartbeat thresholds and calculates the number of signals received by the input device based on the number of times the patient's heartbeat is auscultated over a predetermined amount of time to generate a calculated heart rate; and
   a display connected to the microprocessor that receives the calculated heart rate and outputs the calculated heart rate along with a unique identifier identifying which of the one or more predetermined heartbeat thresholds that the calculated heart rate resides within.

2. The device of claim 1, wherein the predetermined heartbeat thresholds comprise predefined ranges of a newborn's heartbeats per minute.

3. The device of claim 1, wherein the display is activated once the input device has detected heartbeats a predetermined number of times.

4. The device of claim 1, wherein the input device is a component of a stethoscope.

5. The device of claim 1, wherein the display outputs a numerical output that comprises uniquely identified average heartbeats per minute.

6. The device of claim 1, wherein the display outputs a numerical output that comprises average heartbeats per minute, whereby the numerical output changes color depending on where the average heartbeats per minute fall within the one or more predetermined heartbeat thresholds.

7. The device of claim 1, wherein the one or more predetermined heartbeat thresholds are set at whether a patient has less than 60 heartbeats per minute, between 60 and 100 heartbeats per minute or greater than 100 heartbeats per minute.

8. The device of claim 1, wherein the display outputs a different signal output that comprises average heartbeats per minute, whereby the different signal output changes depending on which of the one or more predetermined heartbeat thresholds the average heartbeats per minute fall within.

9. The device of claim 1, wherein the display outputs a combination of a numerical output and a different signal output of average heartbeats per minute, whereby the numerical output and the different signal output change depending on where the average heartbeats per minute fall within the predetermined heartbeat thresholds.

10. A method for calculating a heart rate comprising the steps of:
   placing a stethoscope on a patient;
   providing a device for inputting data each time a heartbeat of the patient is detected, the device comprising:
      an input device that receives a signal each time a heartbeat of a patient is detected;
      a microprocessor coupled to the input device, wherein the microprocessor is programmed with one or more predetermined heartbeat thresholds and calculates the number of signals received by the input device over a predetermined amount of time to generate a calculated heart rate; and
      a display connected to the microprocessor that receives the calculated heart rate and outputs the calculated heart rate along with a unique identifier identifying which of the one or more predetermined heartbeat thresholds that the calculated heart rate resides within;
   an end-user actuating the input device each time the patient's heartbeat is auscultated to generate a number of heartbeat signals, the number of heartbeat signals being generated based on the number of times the patient's heartbeat is auscultated;
   inputting each of the number of heartbeat signals into the microprocessor;
   calculating the heart rate in the microprocessor using the input number of heartbeat signals;
   outputting the calculated heart rate to the display; and
   treating the patient based on which of the one or more predetermined heartbeat thresholds that the calculated heart rate resides within.

11. The method of claim 10, wherein the predetermined heartbeat thresholds comprise predefined ranges of a neonatal patient's heartbeats per minute.

12. The method of claim 10, wherein the predetermined amount of time is at least 0.1 seconds.

13. The method of claim 10, wherein the display is updated with a rolling-average of heartbeats calculated at a select number of heartbeats.

14. The method of claim 10, wherein the display outputs a numerical output that comprises uniquely identified average heartbeats per minute.

15. The method of claim 10, wherein the display outputs a numerical output that comprises uniquely identified average heartbeats per minute, whereby the numerical output changes color depending on where the uniquely identified average heartbeats per minute fall within the one or more predetermined heartbeat thresholds.

16. The method of claim 10, wherein the one or more predetermined heartbeat thresholds are set at whether the patient has less than 60 heartbeats per minute, between 60 and 100 heartbeats per minute or greater than 100 heartbeats per minute.

17. The method of claim 10, wherein the display outputs a different signal output that comprises average heartbeats per minute, whereby the different signal output changes depending on which of the one or more predetermined heartbeat thresholds the average heartbeats per minute fall within.

18. The method of claim 10, wherein the display outputs a combination of a numerical output and a different signal output of average heartbeats per minute, whereby the numerical output and the different signal output change depending on where the average heartbeats per minute fall within the predetermined heartbeat thresholds.

19. A system for providing real-time medical information comprising:

an input device, the input device being actuated each time a heartbeat of a patient is auscultated to generate actuation data;

a microprocessor coupled to the input device and receiving the actuation data from the input device, the microprocessor is programmed with predetermined heartbeat thresholds and calculates the number of times the input device is actuated using the input actuation data over a predetermined amount of time to generate a calculated heart rate;

a display connected to the microprocessor that receives the calculated heart rate and outputs the calculated heart rate along with a unique identifier identifying whether the calculated heart rate is below, at or above any of the predetermined heartbeat thresholds; and treating the patient based on where the calculated heart rate falls within the predetermined heartbeat thresholds.

* * * * *